United States Patent [19]

Suzuki et al.

[11] Patent Number: 5,141,863

[45] Date of Patent: Aug. 25, 1992

[54] PURIFICATION PROCEDURE OF TPA FROM CRUDE PREPARATIONS

[75] Inventors: Katsuyuki Suzuki, Hiroshima; Nobuhiro Kawashima, Sagamihara; Noriko Morii; Kunizou Mori, both of Yokohama, all of Japan

[73] Assignee: Mitsui Toatsu Chemicals, Incorporated, Tokyo, Japan

[21] Appl. No.: 517,383

[22] Filed: May 1, 1990

Related U.S. Application Data

[63] Continuation of Ser. No. 82,141, Aug. 6, 1987, abandoned.

[30] Foreign Application Priority Data

Aug. 11, 1986 [JP] Japan .................. 61-186851

[51] Int. Cl.$^5$ .............................................. C12N 9/64
[52] U.S. Cl. ................................. 435/226; 435/219; 435/815
[58] Field of Search ............... 435/221, 219, 212, 215, 435/217, 183, 814, 815

[56] References Cited

U.S. PATENT DOCUMENTS

| | | | |
|---|---|---|---|
| 3,542,646 | 3/1970 | Aoki et al. | 195/66 |
| 3,904,480 | 9/1975 | Hull et al. | 435/212 |
| 4,898,825 | 2/1990 | Morii et al. | 435/212 |
| 4,928,620 | 12/1990 | Morii et al. | 435/226 |
| 4,960,702 | 10/1990 | Rill et al. | 435/226 |
| 4,985,362 | 1/1991 | Morii et al. | 435/226 |

FOREIGN PATENT DOCUMENTS

| | | | |
|---|---|---|---|
| 0112122 | 6/1984 | European Pat. Off. | 435/226 |
| 1443189 | 7/1976 | United Kingdom. | |

OTHER PUBLICATIONS

Heussen, C., et al., (1984) J. Biol. Chem. 259(19), 11635–11638.
Ritken, D. et al., *J. Biol. Chem.*, vol. 256, pp. 7035–7041, 1981.
Winkler, M. E., et al., (1986) Biochemistry 25, 4041–4045.

*Primary Examiner*—Charles L. Patterson
*Attorney, Agent, or Firm*—Nixon & Vanderhye

[57] ABSTRACT

Tissue plasminogen activator (tPA) species having a specific molecular weight can be isolated in a purified form from a crude tPA preparation containing various tPA species having different molecular weights by bringing the crude tPA preparation into contact with hydroxyapatite and then separately eluting the adsorbed tPA species with eluents having different pHs and/or salt concentrations.

4 Claims, No Drawings

5,141,863

PURIFICATION PROCEDURE OF TPA FROM CRUDE PREPARATIONS

This is a continuation of application Ser. No. 07/082,141 filed Aug. 6, 1987, now abandoned.

BACKGROUND OF THE INVENTION

1) Field of the Invention

This invention relates to a method for the purification of tissue plasminogen activator (tPA), and more specifically to a method for purifying tPA from a crude tPA preparation, which contains various tPA species of different molecular weights and other proteinaceous impurities, by bringing the crude tPA preparation into contact with hydroxyapatite and then separately isolating and purifying tPA species of different molecular weights with eluents, whose pHs and/or salt concentrations have been adjusted in advance, and to which one or more additives may be added if required.

2) Description of the Prior Art

Use of hydroxyapatite for the purification of tPA has itself been known. In a method using hydroxyapatite, in order to obtain tPA from a crude tPA preparation, tPA is adsorbed to the hydroxyapatite, and thereafter eluted from the tPA-bearing hydroxyapatite with ammonia-containing solution (see Japanese Patent Laid-Open No. 76419/1986 for instance). Under conditions employed for the above elution, tPA species of different molecular weights could not be separated from one another and moreover, the activity of tPA might be reduced.

SUMMARY OF THE INVENTION

An object of this invention is to provide a method for isolation of each tPA species from a crude tPA preparation which have different molecular weights and react with an anti-human tPA antibody, whereby throughout all of the purification steps, the activity of tPA is not changed unlike the above-described conventional method. These tPA species include tPA, active degraded products of tPA, polymers of tPA, complexes of tPA and other protein, and the like.

When tPA-producing cells are cultured to obtain tPA, it has been found that the resulting culture broth contains, as proteins reactive with an anti-human tPA antibody, various tPA species having different molecular weights including tPA species having molecular weights of from about 30,000-about 45,000 daltons, tPA species having molecular weights of from about 50,000 to about 70,000 daltons and tPA species having a molecular weight of about 100,000 or higher.

It is therefore the object of the present invention to provide a method for isolating and purifying tPA of a specific molecular weight from various tPA species of different molecular weights and proteinaceous impurities in a mixed state as mentioned above.

The present inventors have carried out an extensive investigation with a view toward fulfilling the above object. As a result, it has been found that the degree of adsorption of tPA to hydroxyapatite is governed by pH and/or salt concentration and also varies depending on the molecular weight of the tPA itself. Namely, the binding strength of tPA to hydroxyapatite becomes greater as the pH decreases or the salt concentration drops. At the same pH and salt concentration, tPA having higher molecular weights is adsorbed more tightly.

The above finding has then led to completion of the method of this invention, in which a variety of tPA species having different molecular weights are adsorbed to hydroxyapatite and then treated with eluents having different pHs and/or salt concentrations so as to isolate a particular tPA species in a-purified form.

In one aspect of this invention, there is thus provided a method for the purification of tPA from a crude tPA preparation containing various tPA species of different molecular weights, which comprises the steps of bringing the crude tPA preparation into contact with hydroxyapatite to adsorb the various tPA species to the hydroxyapatite and then eluting the tPA species with eluents whose pHs and/or salt concentrations are different, thereby isolating the tPA species of the different molecular weights from one another.

Although it has been known to use hydroxyapatite for the purification of proteins, it has not been reported to isolate a particular tPA species from a variety of tPA species as in the method of this invention.

According to the method of this invention, tPA can be recovered up to 90-100% in terms of its activity and can also be isolated into individual tPA species of different molecular weights without need for aqueous ammonia as an eluent for tPA adsorbed on hydroxyapatite unlike conventional techniques.

DETAILED DESCRIPTION OF THE INVENTION

Tissue plasminogen activator (tPA) is produced in the tissue of a higher animal, and is a protein which activates plasminogen, a precursor of plasmin which is a proteolytic enzyme specific to fibrin.

This tPA is produced in a culture medium by culturing human melanoma cells, normal human cells, or cells carrying the human tPA gene integrated according to recombinant DNA technology. tPA obtained in the resulting culture broth comprises a variety of molecular species of tPA.

Crude tPA preparations, to which the method of the present invention can be applied effectively, contains various molecular species produced as described above by way of example. It may be in a form contained in a culture broth or may be in a form obtained by partially purifying a preparation from such a culture broth. This invention is however not limited to them. The method of this invention can be applied to aqueous media each of which contains various tPA species of different molecular weights produced by one of several methods.

In the method of this invention, such crude tPA preparation is first of all brought into contact with hydroxyapatite so as to adsorb the various tPA species to the hydroxyapatite.

No particular limitation is imposed on hydroxyapatite to be used. It is generally possible to use hydroxyapatite which is constituted of calcium phosphate and has been prepared into a desired one of various shapes by one of various preparation processes. Especially, those prepared for use in chromatography are used preferably in many instances.

An aqueous medium containing various tPA species as a crude tPA preparation is brought into contact with such hydroxyapatite so that the tPA species of various different molecular weights are adsorbed. No particular limitation is imposed on conditions for effecting the above contact. The contact may hence be effected by a general column method or a batchwise method. In the column method, an aqueous medium containing the tPA species is caused to flow either upwardly or downwardly through a column packed with hydroxyapatite so that the tPA species are brought into contact with the hydroxyapatite and is hence adsorbed to the hydroxyapatite. In the batchwise method on the other hand, hydroxyapatite and an aqueous medium containing various tPA species are mixed together so as to bring the tPA species into contact with the hydroxyapatite. Various tPA species having different molecular weights, which have been adsorbed to the hydroxyapatite, are thereafter isolated from one another.

In the method of this invention, the pHs and/or salt concentrations of eluents are changed according to a tPA species of a desired molecular weight to be eluted. It may be feasible to add an additive to the eluents so as to accelerate and enhance the elution and isolation of various molecular species.

The lower limit of the pH of an eluent useful in the practice of the method of this invention is the lowest pH at which hydroxyapatite used is still not dissolved. On the other hand, its upper limit is the highest pH at which tPA species of different molecular weights, which are reactive with an anti-human tPA antibody, can still be isolated from one another. An eluent of such a pH range may hence be used, but pH 5-10 is preferred, with pH 6-9 being more preferred.

Furthermore, a salt is used to separate tPA from hydroxyapatite. The salt useful in the practice of the method of this invention is a salt having no chelating ability. It is hence possible to use, for example, a salt containing a kaotropic ion such as a thiocyanate or perchlorate, or a chloride, fluoride, phosphate, carbonate, sulfate, nitrate, borate, acetate or the like. As specific examples of preferred salts, may be mentioned sodium phosphate, potassium phosphate, sodium chloride, potassium chloride, ammonium thiocyanate, sodium sulfate, sodium borate, sodium acetate, etc.

As an additive, a basic amino acid or its derivatives such as arginine, lysine, ornithine or ε-aminocaproic acid may be used at a concentration of 1 mM-0.5M, preferably, 5 mM-0.3M in an eluent. Use of an eluent containing such an additive facilitates the elution further, and also permits more effective isolation of tPA species of different molecular weights.

In order to isolate a desired tPA species from the various tPA species adsorbed on the hydroxyapatite, it is necessary to use an eluent whose pH and/or salt concentration have been adjusted so as to selectively elute the desired tPA species as described above. The eluent may contain an additive, if necessary.

A tPA species having a lower molecular weight is eluted first with subsequent and successive elution of tPA species of higher molecular weights as the pH of an eluent increases from a lower level to a higher level. The salt concentration to be used varies depending not only on the type of the salt but also on the pH of the eluent.

For example, the following relations exist among the pH, the salt concentration and the molecular weight of a tPA species to be isolated.

When an eluent containing a phosphate at a concentration of 0.02-0.1M and having a pH of 6-9 is used, tPA species having molecular weights in a range of from about 30,000 to about 45,000 daltons can be eluted. In other words, in order to isolate the tPA species whose molecular weights range from about 30,000 daltons to about 45,000 daltons, they may be preferably eluted under optimum conditions selected from a phosphate concentration range of 0.02-0.1M and a pH range of 6-9. Thereafter, tPA species whose molecular weights range from about 45,000 daltons to about 70,000 daltons can be eluted at pH 7-9 and phosphate concentrations of 0.03-0.1M. tPA species having molecular weights about 70,000 daltons can be then eluted at pH 6-9 and phosphate concentrations of 0.04-0.3M. Finally, tPA species having molecular weight of about 70,000 daltons and tPA species having molecular weight of about 100,000 daltons and higher can be eluted at pH 6-10 and phosphate concentrations of 0.04-0.5M.

When elution is conducted with an eluent containing sodium chloride, it is preferable to effect the adsorption of tPA species to hydroxyapatite at a NaCl concentration of 0.03M or lower and a pH of 6-8. tPA species whose molecular weights range from about 30,000 daltons to about 45,000 daltons can be eluted at pH 6-9 and NaCl concentrations of 0.03-0.15M. Thereafter, tPA species whose molecular weights range from about 45,000 daltons to about 70,000 daltons can be eluted at pH 7-9 and NaCl concentrations of 0.05-0.15M. tPA species having molecular weights of about 70,000 daltons can be then eluted at pH 6-9 and NaCl concentrations of 0.07-0.7M. Further, tPA species having molecular weights of about 70,000 daltons and about 100,000 daltons and higher can be eluted at pH 6-10 and NaCl concentrations of 0.07-1.0M.

As has been described above, tPA species having desired molecular weights can be isolated and obtained either successively or selectively by using a chosen salt, salt concentration and pH.

The present invention will hereinafter be described by the following Examples.

EXAMPLE 1

After culturing Bowes melanoma cells in RPMI 1640 culture medium (Gibco) supplemented with 10% thermoinactivated (56° C., 30 minutes) fetal calf serum (FCS, Gibco), the cells were collected and washed once. The washed cells were then cultured for 24 hours in a serum-free medium and the resultant culture supernatant was yielded.

Ammonium sulfate was added at a rate of 300 g/l to 2 l of the culture supernatant. The resultant mixture was thereafter adjusted to pH 7.0 and then allowed to stand overnight at 4° C.

The resultant precipitate was collected by centrifugation, dissolved in a 0.01M phosphate buffer (pH 6.0) and then dialyzed against the same buffer so as to desalt the same. The dialyzed solution was then charged into a column of 5 ml of hydroxyapatite which had been equilibrated with a 0.01M phosphate buffer (pH 6.0).

The column effluent was collected and its plasminogen-dependent fibrinolytic activity was measured. No activity was however detected.

Proteins adsorbed were eluted using a 0.03M phosphate buffer (pH 6.0).

The plasminogen-dependent fibrinolytic activity of the eluate was measured. It was found to be 2% of the activity charged into the column.

This eluted fraction was subjected to electrophoresis in an SDS polyacrylamide gel and was then analyzed by a zymography. As a plasminogen activator, bands were observed in a range of about 30,000 daltons-about 45,000 daltons.

The column was then washed with a 0.05M phosphate buffer (pH 7.5). The plasminogen-dependent fibrinolytic activity of the eluate was measured. It was found to be 3% of the activity charged into the column. This eluted fraction was subjected to electrophoresis in an SDS polyacrylamide gel and was then analyzed by a zymography. As a plasminogen activator, bands were observed in a range of from about 45,000 daltons up to about 70,000 daltons.

Subsequently, the column of the hydroxyapatite was treated with a 0.2M phosphate buffer (pH 7.0).

The plasminogen-dependent fibrinolytic activity of the eluate was measured. It was found to be 85% of the activity applied to the column.

This eluted fraction was subjected to electrophoresis in an SDS polyacrylamide gel and was then analyzed by a zymography. As a plasminogen activator, a band was observed at a molecular weight of about 70,000.

Remaining adsorbed proteins were eluted with a 0.4M phosphate buffer (pH 7.5).

The plasminogen-dependent fibrinolytic activity of the eluate was measured. It was found to be 5% of the activity applied to the column.

This eluted fraction was subjected to electrophoresis in an SDS polyacrylamide gel and was then analyzed by a zymography. As plasminogen activators, bands were observed at molecular weights of about 70,000 and 100,000 and higher respectively.

EXAMPLE 2

After stabilizing with 0.02% of "Tween 80" (Junsei Chemicals) 2 l of a culture supernatant prepared from a culture of human fetal foreskin cells, whose culture medium contained 10% of thermoinactivated (56° C., 30 minutes) fetal calf serum and 20 KIU/ml of aprotinin (Bayer), it was charged into a column of anti-human urokinase.

The column effluent was collected and its plasminogen-dependent fibrinolytic activity was measured. About 60% of the activity charged into the column was observed.

This effluent fraction was analyzed by a zymography after subjecting same to electrophoresis in an SDS polyacrylamide gel. Various bands were observed as plasminogen activators in a molecular weight range of from about 30,000 dalton to about 150,000 daltons.

These bands were found to correspond to tPA because they were not affected when treated with an anti-human urokinase but disappeared when treated with an anti-human tPA antibody.

Ammonium sulfate was added at a rate of 300 g/l to this effluent fraction. The resulting solution was adjusted to pH 7.0 and then allowed to stand overnight at 4° C.

The thus-formed precipitate was collected by centrifugation, followed by dialysis against a 0.03M phosphate buffer (pH 6.8).

The dialyzed solution was thereafter charged into a column of 5 ml of hydroxyapatite which had been equilibrated with a 0.03M phosphate buffer (pH 6.8). The column effluent was collected and its plasminogen-dependent fibrinolytic activity was measured. It was found to be about 2% of the activity charged into the column. This effluent fraction was subjected to electrophoresis in an SDS polyacrylamide gel and was then analyzed by a zymography. Bands were observed as tPA in a range of about 30,000 daltons–about 45,000 daltons.

The column was then washed with a 0.05M phosphate buffer (pH 7.8). The plasminogen-dependent fibrinolytic activity of the eluate was measured. It was found to be 5% of the activity charged into the column. tPA species having molecular weights in a range of about 45,000 daltons–about 70,000 daltons were observed on a zymograph.

Proteins thus adsorbed were then eluted with a 0.25M phosphate buffer (pH 6.0). The plasminogen-dependent fibrinolytic activity of the eluate was found to be about 80% of the activity charged into the column. Its molecular weight was found to be about 70,000 daltons on a zymograph.

The remaining adsorbed proteins were eluted with a 0.3M $Na_2HPO_4$-NaOH buffer (pH 10.0).

The plasminogen-dependent fibrinolytic activity of the eluate was measured. It was found to be about 10% of the activity charged into the column. As its molecular weights, bands corresponding to about 70,000 daltons and about 100,000 daltons and higher were observed on a zymograph.

EXAMPLE 3

After stabilizing with 0.02% of "Tween 80", 2 l of a culture supernatant prepared from a culture of Chinese hamster ovary (CHO) cells with human tPA gene integrated therein (CHO Kl ATCC CCL 61) whose culture medium contained 10% of thermoinactivated (56° C., 30 minutes) fetal calf serum and 40 KIU/ml of aprotinin, it was adjusted to pH 5.0 with phosphoric acid.

The resultant solution was charged into a column of 50 ml of carboxymethyl (CM) Sepharose (Pharmacia AB) which had been equilibrated with a 0.05M sodium dihydrogenphosphate buffer (pH 5.0) containing 0.15M of sodium chloride and "Tween 80" (0.02%).

The resin containing proteins adsorbed thereon was washed with a 0.05M phosphate buffer (pH 6.4), followed by elution of tPA with a 0.05M phosphate buffer (pH 6.4) which contained 0.5M of sodium chloride. The plasminogen-dependent fibrinolytic activity of the eluate was measured. About 85% of the activity charged into the column was found to be recovered.

This eluted fraction was analyzed by a zymography after subjecting same to electrophoresis in an SDS polyacrylamide gel. Various bands were recognized as tPA in a molecular weight range of about 30,000 daltons—about 150,000 daltons.

The eluate was diluted tenfold to water and then charged into a column of 5 ml of hydroxyapatite which had been equilibrated with a 5 mM sodium phosphate buffer (pH 6.4) containing 0.05M of sodium chloride. The column effluent was collected and its plasminogen-dependent fibrinolytic activity was measured. It was found to be about 3% of the activity charged into the column. This effluent fraction was subjected to electrophoresis in an SDS acrylamide gel and was then analyzed by a zymography. As a plasminogen activator, bands were observed in a range of about 30,000 daltons–about 45,000 daltons.

The column was then eluted with a 5 mM phosphate buffer (pH 7.4) containing 0.08M of sodium chloride. About 7% of the activity charged into the column was measured. This eluted fraction exhibited bands corresponding to molecular weights of about 45,000–about 70,000 on a zymograph. The column was then treated with a 5 mM phosphate buffer (pH 7.8) which contained 0.3M of sodium chloride. The activity of the eluate was found to amount to about 80% of the activity charged into the column. This eluate exhibited a band corresponding to a molecular weight of about 70,000 daltons on a zymograph.

The remaining adsorbed proteins were eluted with a 5 mM phosphate buffer (pH 7.8) which contained 0.5M of sodium chloride. The activity of the eluate was about 10% of the activity charged into the column. This eluate exhibited bands corresponding to molecular weights of about 70,000 daltons and about 100,000 daltons and higher respectively on a zymograph.

EXAMPLE 4

Two liters of a culture supernatant prepared from a culture of mouse fibroblast cells (C127, ATCC CRL 1616) transformed by the human tPA gene (U.S. patent application Ser. No. 932,209), whose culture medium contained 2% of thermoinactivated (56° C., 30 minutes) fetal calf serum and 40 KIU/ml of aprotinine, were stabilized with "Tween 80 (0.02%)".

The resulting solution was charged into a column of 50 ml of anti-human tPA antibody Sepharose equilibrated with a 0.1M aqueous solution of ammonium bicarbonate (pH 8.0) which contained 0.15M of sodium chloride and "Tween 80 (0.02%)".

After washing the thus-adsorbed proteins with a 0.1M aqueous solution of ammonium bicarbonate (pH 8.0) which contained 2.0M of sodium chloride and "Tween 80 (0.02%)", the proteins were eluted with a 0.1M aqueous solution of ammonium bicarbonate (pH 8.0) which contained 2.0M ammonium thiocyanate and "Tween 80 (0.02%)".

The plasminogen-dependent fibrinolytic activity of the eluate was measured. It was found to be about 90% of the activity charged into the column.

This eluted fraction was subjected to electrophoresis in an SDS polyacrylamide gel and then analyzed by a zymography. Various bands were recognized as tPA in a molecular weight range of about 30,000 daltons–about 150,000 daltons.

This eluate was diluted twentyfold to water and then adjusted to pH 7.5. The resulting solution was then charged into a column of 5 ml of hydroxyapatite which had been equilibrated with a 5 mM aqueous solution of ammonium bicarbonate (pH 7.5) containing 0.1M of ammonium thiocyanate, followed by washing of the column with the same buffer as that used for the above equilibration.

The column effluent was collected. Its plasminogen-dependent fibrinolytic activity was measured. It was found to be about 5% of the activity charged into the column. This effluent exhibited bands in a molecular weight range of about 30,000 daltons–about 70,000 daltons on a zymograph.

The column was then treated with a 0.1M aqueous solution of ammonium bicarbonate (pH 8.0) which contained 0.2M ammonium thiocyanate. The activity of the eluate was about 90% of the activity charged into the column. This eluate exhibited a band corresponding to a molecular weight of about 70,000 daltons on a zymograph.

The column was washed further with a 0.1M aqueous solution of ammonium bicarbonate (pH 8.0) which contained 0.5M of ammonium thiocyanate. In the thus-obtained eluate, about 5% of the activity charged into the column was measured. This eluate exhibited bands corresponding to molecular weights of about 70,000 daltons and 100,000 daltons and higher respectively on a zymograph.

EXAMPLE 5

Ammonium sulfate was added at a rate of 300 g/l to 2 l of a culture supernatant prepared from a culture of human fetal amniotic cells (FL, ATCC CCL-62) carrying the human tPA gene associated with human cytomegalovirus (HCMV) as a promoter for human tPA expression, whose culture medium contained 2% of thermoinactivated (56° C., 30 minutes) fetal calf serum and 20 KIU/ml of aprotinin. The resulting mixture was adjusted to pH 7.0 and then allowed to stand overnight at 4° C.

The thus-formed precipitate was collected by centrifugation, followed by dialysis against a 0.04M phosphate buffer (pH 8.0) containing 10 mM of arginine so as to desalt the precipitate.

The resulting dialyzed solution was charged into a column of 5 ml of hydroxyapatite equilibrated with a 0.04M phosphate buffer (pH 8.0) containing 10 mM of arginine. The column was washed with the same buffer as that employed for the equilibration.

The column effluent was then collected and its plasminogen-dependent fibrinolytic activity was measured. It was found to be about 5% of the activity charged into the column. This effluent exhibited bands in a molecular weight range of about 30,000 daltons–about 70,000 daltons on a zymograph.

The column was then treated with a 0.20M phosphate buffer (pH 6.0) which contained 50 mM of arginine. The activity of the eluate was about 90% of the activity charged into the column. This eluate exhibited a band corresponding to a molecular weight of about 70,000 daltons on a zymograph.

When the column was thereafter washed with a 0.5M phosphate buffer (pH 7.8) containing 50 mM of arginine, about 5% of the activity charged into the column was measured. This eluted fraction exhibited bands corresponding to molecular weights of about 70,000 daltons and about 100,000 daltons and higher on a zymograph.

EXAMPLE 6

Host cells (*Saccharomyces cerevisiae*) transformed with the human tPA gene therein were allowed to grow by a known method, namely, by the method described in Principles and Practice of Recombinant DNA Research with Yeast in The Molecular Biology of Yeast Saccharomyces: Metabolism and Gene Expression, pp 603–636, Cold Spring Harbor Laboratory, Cold Spring Harbor, N.Y. (1982). The resultant cells were ground with glass beads. tPA was extracted with a 0.01M phosphate buffer (pH 7.0) which contained 50 mM of lysine, 1.0M sodium chloride and 0.02% of "Tween 80". The resulting liquid mixture was filtered to collect a filtrate.

The filtrate was diluted tenfold in a 0.01M phosphate buffer (pH 7.5) and was then charged into a column of 5 ml of hydroxyapatite equilibrated with a 0.01M phosphate buffer (pH 7.0) which contained 5 mM of lysine and 0.1M of sodium chloride. The column was washed with the same buffer as that employed for the equilibration.

The column effluent was collected and its plasminogen-dependent fibrinolytic activity was measured. About 15% of the activity charged into the column was found. This effluent exhibited bands in a molecular weight range of about 30,000 daltons–about 70,000 daltons on a zymograph.

The thus-adsorbed proteins were eluted with a 0.20M phosphate buffer (pH 6.5) which contained 5 mM of lysine. The activity of the eluate was about 80% of the activity charged into the column. This eluate exhibited a band corresponding to a molecular weight of about 70,000 daltons on a zymograph.

The column was washed with a 0.5M phosphate buffer (pH 7.8) containing 5 mM of lysine. The thus-obtained eluate contained about 5% of the activity charged into the column. This eluate exhibited bands corresponding to molecular weights of about 70,000 daltons and about 100,000 daltons and higher respectively on a zymograph.

As hydroxyapatite, HCA-100S (Mitsui Toatsu Chemicals, Inc.), in Examples 1 and 2; HA-ultrogel (LKB), in Examples 3 and 4; and Bio gel-HT (Bio Rad), in Examples 5 and 6 were used.

What is claimed is:

1. A method of separating a mixture of tissue plasminogen activator (tPA) having different molecular weights of not less than 30,000 daltons into fraction (1) containing tPA species having molecular weights ranging from about 30,000 to about 45,000 daltons; fractions (2) containing tPA species having molecular weights ranging from about 45,000 to about 70,000 daltons; fraction (3) containing tPA species having a molecular weight of about 70,000 daltons; and fraction (4) containing tPA species having molecular weights not less than about 100,000 daltons, which method comprises the steps of:
   (a) contacting said mixture of tPA species with hydroxyapatite to adsorb said tPA species having different molecular weights of not less than 30,000 daltons, and then
   (b) treating said hydroxyapatite with eluants to elute said fractions (1)–(4) successively, said eluants being different in pH, salt concentrations or both pH and salt concentrations so as to fractionally elute said fractions (1)–(4).

2. The method as claimed in claim 1, wherein at least one of the eluants contains at least one substance selected from the group consisting of basic amino acids, arginine, lysine, ornithine and ε-aminocaproic acid.

3. The method as claimed in claim 2, wherein said eluant contains from about 1 mM to about 0.5M of said substance.

4. The method as claimed in claim 3, wherein said eluant contains from about 5 mM to about 0.3M of said substance.

* * * * *